(12) United States Patent
Roby et al.

(10) Patent No.: US 7,901,705 B2
(45) Date of Patent: Mar. 8, 2011

(54) ANTIMICROBIAL RELEASING POLYMERS

(75) Inventors: Mark Roby, Killingworth, CT (US);
John Kennedy, Guilford, CT (US);
Joshua B. Stopek, Yalesville, CT (US);
Brian Cuevas, Cumming, GA (US);
Nadya Belcheva, Middletown, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 547 days.

(21) Appl. No.: 11/712,334

(22) Filed: Feb. 28, 2007

(65) Prior Publication Data
US 2007/0224162 A1 Sep. 27, 2007

Related U.S. Application Data

(60) Provisional application No. 60/777,430, filed on Feb. 28, 2006.

(51) Int. Cl.
*A61F 2/02* (2006.01)
(52) U.S. Cl. ........................................ 424/426
(58) Field of Classification Search .................. None
See application file for complete search history.

(56) References Cited

U.S. PATENT DOCUMENTS

| | | |
|---|---|---|
| 3,187,752 A | 6/1965 | Glick |
| 3,565,077 A | 2/1971 | Glick |
| 4,014,973 A | 3/1977 | Thompson |
| 4,024,871 A | 5/1977 | Stephenson |
| 4,043,344 A | 8/1977 | Landi et al. |
| 4,047,533 A | 9/1977 | Perciaccante et al. |
| 4,201,216 A | 5/1980 | Mattei |
| 5,019,093 A | 5/1991 | Kaplan et al. |
| 5,059,213 A | 10/1991 | Chesterfield et al. |
| 5,133,738 A | 7/1992 | Korthoff et al. |
| 5,181,923 A | 1/1993 | Chesterfield et al. |
| 5,226,912 A | 7/1993 | Kaplan et al. |
| 5,256,765 A | 10/1993 | Leong |
| 5,261,886 A | 11/1993 | Chesterfield et al. |
| 5,306,289 A | 4/1994 | Kaplan et al. |
| 5,318,575 A | 6/1994 | Chesterfield et al. |
| 5,370,031 A | 12/1994 | Koyfman et al. |
| 5,383,387 A | 1/1995 | Chesterfield et al. |
| 5,518,730 A * | 5/1996 | Fuisz .......................... 424/426 |
| 5,616,338 A | 4/1997 | Fox, Jr. et al. |
| 5,662,682 A | 9/1997 | Chesterfield et al. |
| 5,667,528 A | 9/1997 | Colligan |
| 5,716,376 A | 2/1998 | Roby et al. |
| 5,772,640 A | 6/1998 | Modak et al. |
| 5,985,990 A | 11/1999 | Kantner et al. |
| 6,054,504 A | 4/2000 | Dalla Riva Toma |
| 6,083,208 A | 7/2000 | Modak et al. |
| 6,106,505 A | 8/2000 | Modak et al. |
| 6,129,782 A | 10/2000 | Brodie et al. |
| 6,191,236 B1 | 2/2001 | Roby et al. |
| 6,203,564 B1 | 3/2001 | Hutton et al. |
| 6,224,579 B1 | 5/2001 | Modak et al. |
| 6,299,651 B1 | 10/2001 | Li |
| 6,451,748 B1 | 9/2002 | Taylor et al. |
| 6,475,505 B1 | 11/2002 | Stadler |
| 6,545,097 B2 | 4/2003 | Pinchuk et al. |
| 6,589,591 B1 | 7/2003 | Mansouri et al. |
| 6,596,403 B2 | 7/2003 | Mitra et al. |
| 6,596,657 B1 | 7/2003 | Shalaby |
| 6,640,371 B2 | 11/2003 | Green et al. |
| 6,706,024 B2 | 3/2004 | Modak et al. |
| 7,186,789 B2 * | 3/2007 | Hossainy et al. .............. 528/272 |
| 2002/0165112 A1 | 11/2002 | Kwon et al. |
| 2003/0018306 A1 | 1/2003 | Bucay-Couto et al. |
| 2003/0078242 A1 | 4/2003 | Raad et al. |
| 2003/0096017 A1 | 5/2003 | Decker et al. |
| 2003/0109492 A1 | 6/2003 | Loftsson |
| 2003/0157193 A1 | 8/2003 | McDonald et al. |
| 2003/0203991 A1 | 10/2003 | Schottman et al. |
| 2003/0224033 A1 | 12/2003 | Li et al. |
| 2004/0068293 A1 | 4/2004 | Scalzo et al. |
| 2004/0068294 A1 | 4/2004 | Scalzo et al. |
| 2004/0162580 A1 | 8/2004 | Hain |
| 2006/0013851 A1 | 1/2006 | Giroux |

FOREIGN PATENT DOCUMENTS

| | | |
|---|---|---|
| EP | 0 499 048 A1 | 8/1992 |
| WO | WO 96/22114 A1 | 7/1996 |
| WO | WO 97/14447 A1 | 4/1997 |
| WO | WO 98/00065 | 1/1998 |
| WO | WO 00/57933 | 10/2000 |
| WO | WO 00/65024 A2 | 11/2000 |
| WO | WO 01/52805 A1 | 7/2001 |
| WO | WO 03/011173 | 2/2003 |
| WO | WO 03/093357 A1 | 11/2003 |
| WO | WO 2004/045663 | 6/2004 |
| WO | WO 2004/045663 A1 | 6/2004 |
| WO | WO 2004/066927 | 8/2004 |

OTHER PUBLICATIONS

International Search Report for PCT/US2007/05236 date of completion is Aug. 29, 2008 (9 pages).
International Search Report from Application EP 06 01 2688 dated Oct. 9, 2007.
International Search Report from Application PCT/US07/04477 dated Jul. 7, 2008.

* cited by examiner

*Primary Examiner* — Carlos A Azpuru

(57) ABSTRACT

The present disclosure is directed to polymers having hydroxyl containing bioactive agents incorporated into the backbone of the polymer or attached thereto by pendant linkages. Hydroxyl containing bioactive agents which may be attached to these polymers include antimicrobial agents such as triclosan. The polymers may be utilized to form medical devices or coatings for such devices. The hydroxyl containing bioactive agent may be released from the polymer upon hydrolysis of the polymeric backbone or pendant linkage in vivo.

11 Claims, No Drawings

ANTIMICROBIAL RELEASING POLYMERS

CROSS-REFERENCE TO RELATED APPLICATIONS

This application claims the benefit of and priority to U.S. Provisional Patent Application No. 60/777,430 filed Feb. 28, 2006, the entire disclosure of which is incorporated be reference herein.

TECHNICAL FIELD

The present disclosure relates to polymers suitable for use in forming medical devices or coatings thereon. More particularly, the present disclosure relates to polymers capable of releasing bioactive agents, such as antimicrobial agents, in vivo.

DESCRIPTION OF RELATED ART

Biodegradable materials, including synthetic polymeric materials, are known to those skilled in the art for a variety of uses, particularly those uses in which the biodegradable material is implanted within a living organism for medical purposes. The term "biodegradable" is generally used to describe a material capable of being broken down into smaller constituents which can be metabolized and/or excreted by a living organism. Hydrolysis is one mechanism by which many biodegradable materials are broken down following implantation within a living organism. Synthetic polymers that are hydrolytically unstable and hence biodegradable include polymers derived from one or more of glycolide, lactide, p-dioxanone, epsilon-caprolactone and/or trimethylene carbonate. Medical devices (e.g., sutures, clips, pins, etc.) made from such materials may be useful for temporarily holding tissues in a desired position during healing, and being absorbed by the organism after a period of time.

The use of antimicrobial agents in coatings on medical devices such as sutures can be desirable in some instances to reduce infection and promote healing. However, if the coating is removed by handling or use of the device, or if the antimicrobial agent is volatile, coated medical devices may not provide effective levels of antimicrobial activity for a sufficient period of time. If the antimicrobial agent is incorporated into the material from which the medical device is made, the distribution of the antimicrobial agent within the material can be difficult to control and may be affected by processes (e.g., molding, stretching, annealing, and the like) used to form the medical device. Uneven distribution of the antimicrobial agent within the device may not provide the desired release profile of the antimicrobial agent upon in vivo implantation.

Accordingly, there is a need for medical devices that provide predictable antimicrobial efficacy.

SUMMARY

The present disclosure provides bioactive polymers which may be useful in forming medical devices. The bioactive polymer includes at least one hydroxyl containing bioactive agent incorporated in a biodegradable polymer backbone, or attached to a polymer by a pendant linkage. The hydroxyl containing bioactive agent, such as a hydroxyl containing antimicrobial agent, is released as the biodegradable polymer or pendant linkage degrades in vivo. In some embodiments triclosan is the antimicrobial agent utilized to form the bioactive polymer.

The bioactive polymers of the present disclosure may be utilized to form medical devices or coatings thereon.

DETAILED DESCRIPTION

Polymers are described herein having at least one hydroxyl containing bioactive agent bonded thereto, wherein the bioactive agent is released in vivo upon hydrolysis of the polymer. As used herein, a "bioactive polymer" is a polymer having at least one hydroxyl containing bioactive agent bound thereto. As used herein, the terms "bioactive agent" and "hydroxyl containing bioactive agent" are used interchangeably to describe a compound having biological activity in vivo and at least one hydroxyl group capable of linking the bioactive agent to the bioactive polymer. In some embodiments the bioactive agent may be incorporated into the backbone of the polymer, in which case the polymer can advantageously be a biodegradable polymer capable of releasing the bioactive agent upon degradation of the polymer in vivo. In other embodiments, the bioactive agent may be linked to the polymer through a biodegradable pendant linkage. The pendant linkage degrades in vivo, thereby releasing the bioactive agent from the polymer.

Any polymer utilized in surgical or medical applications may be utilized in accordance with the present disclosure. In some embodiments, the polymer may be biodegradable. Such polymers are within the purview of those skilled in the art and include, but are not limited to, absorbable polymers made from glycolide, glycolic acid, lactide, lactic acid, caprolactone, dioxanone, trimethylene carbonate, dimethyl trimethylene carbonate, block or random copolymers thereof, and combinations thereof including mixtures and blends thereof. Other biodegradable materials which may be utilized include, but are not limited to, collagen, chitin, chitin derivatives (e.g., chitosan), amino acid polymers (e.g., gelatin), degradable polyurethanes, polyalkylene oxide initiated block copolymers, polysaccharides (e.g., dextran), and combinations thereof.

In some embodiments, the biodegradable polymer may include a polyalkylene oxide initiated block copolymer having one block made from hard phase forming monomers, i.e. an "A" block, and another block made from random copolymers of soft phase forming monomers, i.e., a "B" block, which are randomly copolymerized. These two specific types of blocks can advantageously be combined to form a block copolymer. The block copolymers may have repeating block units such as AB, ABA, ABAB, ABCBA, BABA, BACAB, etc.

Weight-average molecular weights (Mw) of the polymers which may be utilized in forming the bioactive polymers of the present disclosure may vary from about 2,000 to about 200,000 daltons, in embodiments from about 3,500 to about 100,000 daltons and, in other embodiments, from about 5,000 to about 20,000 daltons. Number average molecular weights (Mn) can also vary widely, but may be from about 1,000 to 100,000, in embodiments from about 2,000 to 50,000 and, in other embodiments, from about 2,500 to about 10,000. Intrinsic viscosities may vary from about 0.01 to about 2.0 dL/g in chloroform at 40° C., in embodiments from about 0.1 to about 1.0 dL/g and, in other embodiments, from about 0.2 to about 0.5 dL/g.

As noted above, in some embodiments the bioactive agent may be incorporated in the polymeric backbone. Methods for incorporating the bioactive agents into a polymeric backbone are within the purview of those skilled in the art. In one embodiment the hydroxyl containing bioactive agent may be incorporated into the polymer backbone during synthesis, and released therefrom during degradation. For example, a degradable polyurethane may be utilized as the polymer, in which case the hydroxyl containing bioactive agent may be incorporated in the polymeric backbone. Similarly, a degradable poly(phosphoester) may be utilized as the polymer, in which case the hydroxyl containing bioactive agent bioactive agent may become part of the poly(phosphoester) backbone.

In other embodiments of the present disclosure, the hydroxyl containing bioactive agent may be attached or linked to the polymer utilizing pendant linkages. Where the bioactive agent is linked to the polymeric chain using pendant linkages, the polymer may be a biodegradable polymer as described above or a non-absorbable polymer. Suitable non-absorbable or more permanent polymeric materials which may be utilized include polyesters (e.g., polyalkyl terephthalates), polyamides (e.g., nylon), polyurethanes, polycarbonates, polyamides, fluoropolymers, polyolefins, vinyl polymers, combinations thereof, and the like.

Pendant biodegradable linkages which may result from the reaction of the hydroxyl containing bioactive agent with the polymer to form a pendant linkage include, for example, ether linkages, ester linkages, urethane linkages, acetal linkages, combinations thereof, and the like. Other illustrative biodegradable linkages which may result from the reaction of the hydroxyl containing bioactive agent with the polymer to form pendant linkage include amide, carbonate, and phosphoester. The hydroxy group of the hydroxyl containing bioactive agent may react with a pendant group on the polymer backbone thereby forming the biodegradable linkage linking the bioactive agent to the polymer. The linkage may degrade by hydrolysis in vivo, releasing the bioactive agent from the polymer.

Methods for attaching hydroxyl containing bioactive agents to the polymer with pendant groups will depend upon the polymer and pendant groups chosen. For example, in some embodiments the polymer may include polymer chains made at least in part from one or more amino acids having a pendant group which provides a site at which a hydroxyl containing bioactive agent may be attached. Suitable amino acids include, for example, serine, threonine, aspartic acid, glutamic acid, arginine, lysine, cysteine, cystine, tyrosine and methionine, asparagine, glutamine, phenylalanine, tryptophan, praline, histidine, combinations thereof, and the like. The precise composition of the polyamino acid chains may vary widely provided that a sufficient number of pendant group-containing amino acids are incorporated into the chain to provide the desired attachment of the bioactive agent. The polymer chain may include a variety of amino acids, or other monomers in combination with amino acids. Such other monomers which may be employed include those known to provide absorbable polymers, such as, for example, glycolide, lactide, caprolactone, alkylene carbonates, alkylene oxides, combinations thereof, and the like. Thus, a polyamino acid chain may be a homopolymer or copolymer (random, block or graft). The amount of pendant group-containing amino acids in the polyamino acid chains may be from about 5 to about 100%.

Regardless of the pendant linkage utilized, the bioactive agent/polymer linkage will degrade in vivo (e.g., via hydrolysis), thereby releasing the bioactive agent from the polymeric backbone.

In other embodiments, biodegradable network structures may be prepared by placing covalent or non-covalent bonds within the network structure that can be broken under biologically relevant conditions. This may involve the use of two separate structural motifs. The degradable structure in combination with the bioactive agent may be either placed into the polymer backbone or into a cross-linker structure. For example, a water soluble linear copolymer containing PEG, glycolic acid and fumaric acid linkages may be prepared. The fumaric acid allows the linear polymer to be cross-linked through free radical polymerization in a second network-forming polymerization step, thus creating a polymer network which may degrade through hydrolysis of the glycolic ester linkages. By adding a hydroxyl containing bioactive agent to the crosslinker, the bioactive agent may also be incorporated into the polymeric network; the bioactive agent may be subsequently released from the network upon hydrolysis of the glycolic ester linkages. Other crosslinkers which may be utilized and linked to a bioactive agent include, for example, a degradable region containing one or more groups such as anhydride, an orthoester, a phosphoester, combinations thereof, and the like.

In some cases, a combination of more than one bioactive agent can be incorporated into the compositions of the present disclosure. This can be accomplished, for example, by incorporating a first bioactive agent into the polymeric backbone and a second bioactive agent by pendant attachment. In other embodiments, a combination of bioactive agents may be delivered by providing mixtures of different polymers which have different agents incorporated into the backbone or attached via pendant positions. The bioactive polymers of the present disclosure can, in some embodiments, be characterized by a release rate of the biologically active substance in vivo that is controlled, at least in part, as a function of hydrolysis of the polymer or pendant linkage during biodegradation.

The rate of hydrolytic degradation, and thus of bioactive agent release, can be altered from minutes to months by altering the physico-chemical properties of the bonds between the bioactive agent and the polymer. The rate of release can be affected by the nature of the bond; stereochemical control, i.e., by building in varying amounts of steric hindrance around the bonds which are to be hydrolyzed; electronic control, i.e., by building in varying electron donating/accepting groups around the reactive bond, thereby controlling reactivity by induction/resonance; varying the hydrophilicity/hydrophobicity of linking groups between the bioactive agent and the polymer backbone; varying the length of the linking groups, e.g., increasing their length will result in the bond to be hydrolyzed being more accessible to water; and/or using bonds susceptible to attack by enzymes present in the environment in which the device is placed.

Moreover, where the polymer is a biodegradable polymer, its degradation in vivo will depend, at least in part, upon its molecular weight, crystallinity, biostability, and the degree of crosslinking. In general, the greater the molecular weight, the higher the degree of crystallinity, and the greater the biostability, the slower the biodegradation of a biodegradable polymer.

Suitable hydroxyl containing bioactive agents which may be attached to, or incorporated into the backbones of, the polymers of the present disclosure include antimicrobial agents, such as antiseptics, and/or disinfectants. Where the bioactive agent is an antimicrobial agent, the antimicrobial agent may be released into the tissue surrounding the polymer and can be utilized to aid in combating clinical and sub-clinical infections in a surgical or trauma wound site.

Illustrative, non-limiting examples of antiseptics and disinfectants which may be utilized as the antimicrobial agent include halo-substituted phenolic compounds like PCMX (i.e., p-chloro-m-xylenol) and triclosan (i.e., 2,4,4'-trichloro-2'-hydroxydiphenyl ether), alcohols, combinations thereof, and the like. In embodiments, at least one of the bioactive agents may be an antiseptic such as triclosan.

The biologically active substances added to the polymer may be included in amounts that are therapeutically effective. While the effective amount of a biologically active substance added to the polymer will depend on the particular agent and polymer being utilized, the biologically active substance may be present in amounts from about 1% to about 65% by weight of the polymer/bioactive agent combination. Lesser amounts may be used to achieve efficacious levels of treatment for certain biologically active substances. In embodiments, the bioactive agent may be present in an amount from about 1% to about 80% by weight of the polymer/bioactive agent combination, in other embodiments from about 5% to about 50% by weight of the polymer/bioactive agent combination.

In some embodiments, the polymers of the present disclosure may also include additional medicinal agents instead of, or in combination with, the bioactive agent. Such medicinal agents may include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antifungals; antivirals; anticoagulants; anticonvulsants; antidepressants; antihistamines; immunological agents, and combinations thereof.

In other embodiments, additional medicinal agents which may be included in the polymer include viruses and cells, peptides (e.g., luteinizing-hormone-releasing-hormone analogues, such as goserelin and exendin) and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons ($\beta$-IFN, ($\alpha$-IFN and $\gamma$-IFN), erythropoietin, nucleases, tumor necrosis factor, colony stimulating factors (e.g., GCSF, GM-CSF, MCSF), insulin, enzymes (e.g., superoxide dismutase, tissue plasminogen activator), tumor suppressors, blood proteins, gonadotropins (e.g., FSH, LH, CG, etc.), hormones and hormone analogs (e.g., growth hormone, adrenocorticotropic hormone and luteinizing hormone releasing hormone (LHRH)), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; ribozymes; and combinations of the foregoing.

The amount of medicinal agent present will depend upon the particular medicinal agent chosen, but may be present, in embodiments, from about 0.01% to about 10% by weight of the polymer composition.

The polymers of the present disclosure may be used to form a variety of surgical devices which may be used for implantation, injection, or otherwise placed totally or partially within the body. Surgical and medical articles which may be prepared utilizing the polymer/bioactive agent of the present disclosure include, but are not necessarily limited to: burn dressings; wound dressings; hernia patches; medicated dressings; fascial substitutes; gauze, fabric, sheet, felt or sponge for liver hemostasis; gauze bandages; arterial grafts or substitutes; bandages for skin surfaces; suture knot clips; orthopedic pins, clamps, screws, and plates; clips (e.g., for vena cava); staples; fasteners including hooks, buttons, and snaps; bone substitutes (e.g., mandible prosthesis); intrauterine devices (e.g., spermicidal devices); draining or testing tubes or capillaries; surgical instruments; vascular implants or supports; anastomosis rings; vertebral discs; extracorporeal tubing for kidney and heart-lung machines; artificial skin; catheters; sutures; drug delivery devices; adhesives; sealants; scaffoldings for tissue engineering applications, and the like.

Biodegradable medical devices and drug delivery products can be prepared in several ways. The polymer in combination with the bioactive agent can be melt processed using conventional extrusion or injection molding techniques, or these products can be prepared by dissolving in an appropriate solvent, followed by formation of the device, and subsequent removal of the solvent by evaporation or extraction.

Once a medical device is in place, it may remain in at least partial contact with a biological fluid, such as blood, internal organ secretions, mucus membranes, cerebrospinal fluid, and the like.

As a structural medical device, the bioactive polymer compositions of the present disclosure provide a physical form having specific chemical, physical, and mechanical properties sufficient for the application and a composition that degrades in vivo into non-toxic residues.

In other embodiments, the bioactive polymer of the present disclosure may be applied as a coating to a medical device. Suitable medical devices which may be coated with the polymer of the present disclosure include all those devices described above such as, for example, surgical needles, staples, clips, drug delivery devices, stents, pins, screws, and fibrous surgical articles such as sutures, prosthetic ligaments, prosthetic tendons, woven mesh, gauze, dressings, growth matrices and the like.

The bioactive polymers may be applied as a coating using conventional techniques. For example, the bioactive polymers may be solubilized in a dilute solution of a volatile organic solvent, e.g. acetone, methanol, ethyl acetate, toluene, combinations thereof, and the like, and then the article can be immersed in the solution to coat its surface. Once the surface is coated, the surgical article can be removed from the solution where it can be dried at an elevated temperature until the solvent and any residual reactants are removed.

Where the bioactive polymer of the present disclosure is applied in solution, the amount of solvent utilized can be from about 15% to about 99% by weight, in embodiments from about 60% to about 98% by weight, of the solution utilized to apply the polymer of the present disclosure, including the bioactive agent, and any additional medicinal agents or adjuvants. In some embodiments the solvent may be present at about 95% by weight of the solution utilized to apply the bioactive polymer of the present disclosure.

In addition, the bioactive polymer of the present disclosure may be combined with other biocompatible polymers, so long as they do not interfere undesirably with the biodegradable characteristics of the composition. Blends of the bioactive polymer of the disclosure with such other polymers may offer even greater flexibility in designing the precise release profile desired for targeted drug delivery or the precise rate of biodegradability desired for structural implants. Examples of such additional biocompatible polymers include other polycarbonates, polyesters, polyorthoesters, polyamides, polyurethanes, poly(iminocarbonates), polyanhydrides, combinations thereof, and the like.

It will be understood that various modifications may be made to the embodiments disclosed herein. For example, in addition to medical devices intended for implantation, it is also contemplated that surgical instruments (including but not limited to endoscopic instruments) can be made of or coated with the bioactive polymers of this disclosure. Thus, in some embodiments the present bioactive polymers may be utilized in the fabrication or coating of surgical instruments. Therefore the above description should not be construed as limiting, but merely as exemplifications of preferred embodiments. Those skilled in the art will envision other modifications within the scope and spirit of the claims appended hereto.

What is claimed is:

1. A bioactive polymer comprising at least one hydroxyl containing antimicrobial agent incorporated in a biodegradable polymer backbone, wherein the antimicrobial agent is released as the biodegradable polymer degrades in vivo.

2. The bioactive polymer of claim 1, wherein the biodegradable polymer backbone includes at least one monomer selected from the group consisting of glycolide, glycolic acid, lactide, lactic acid, caprolactone, dioxanone, trimethylene carbonate, dimethyl trimethylene carbonate, copolymers thereof, and combinations thereof.

3. The bioactive polymer of claim 1, wherein the hydroxyl containing antimicrobial agent is selected from the group consisting of p-chloro-m-xylenol, triclosan and alcohols.

4. The bioactive polymer of claim 1, wherein the antimicrobial agent comprises triclosan.

5. A bioactive polymer comprising a polymer backbone, at least one hydroxyl containing antimicrobial agent, and a biodegradable linkage attaching the at least one hydroxyl containing antimicrobial agent to the polymer backbone, wherein the hydroxyl containing antimicrobial agent is released from the polymer backbone as the biodegradable linkage degrades in vivo.

6. The bioactive polymer of claim 5, wherein the polymer backbone comprises a biodegradable polymer.

7. The bioactive polymer of claim 5, wherein the polymer backbone is at least partially formed from at least one monomer selected from the group consisting of glycolide, glycolic acid, lactide, lactic acid, caprolactone, dioxanone, trimethylene carbonate, dimethyl trimethylene carbonate, copolymers thereof, and combinations thereof.

8. The bioactive polymer of claim 5, wherein the polymer backbone is at least partially formed from a polymer selected from the group consisting of polyesters, polyamides, polyurethanes, polycarbonates, polyamides, fluoropolymers, polyolefins, vinyl polymers, and combinations thereof.

9. The bioactive polymer of claim 5, wherein the hydroxyl containing antimicrobial agent is selected from the group consisting of p-chloro-m-xylenol, triclosan, and alcohols.

10. The bioactive polymer of claim 5, wherein the hydroxyl containing antimicrobial agent comprises triclosan.

11. The bioactive polymer of claim 5, wherein the biodegradable linkage is selected from the group consisting of ethers, esters, urethanes, and acetals.

* * * * *